United States Patent [19]
Neumaier et al.

[11] 3,931,333
[45] Jan. 6, 1976

[54] PRODUCTION OF HALOGEN-CONTAINING TERTIARY PHOSPHINE OXIDES

[75] Inventors: Hubert Neumaier, Knapsack; Manfred Finke, Fischbach; Richard Schüller, Cologne-Holweide, all of Germany

[73] Assignee: Hoechst Aktiengesellschaft, Frankfurt, Germany

[22] Filed: June 21, 1974

[21] Appl. No.: 481,815

[30] Foreign Application Priority Data

Sept. 19, 1973 Germany............................ 2347109

[52] U.S. Cl............................................ 260/606.5 P
[51] Int. Cl.²........................................ C07F 9/02
[58] Field of Search............................ 260/606.5 P

[56] References Cited
UNITED STATES PATENTS

| | | | |
|---|---|---|---|
| 3,306,937 | 2/1967 | Clampitt et al............... | 260/606.5 P |
| 3,716,580 | 2/1973 | Maier....................... | 260/606.5 P |

FOREIGN PATENTS OR APPLICATIONS

| | | |
|---|---|---|
| 1,064,511 | 9/1959 | Germany |
| 192,811 | 1967 | U.S.S.R. |

OTHER PUBLICATIONS

Petrov et al., Russian Chemical Reviews, Vol. 37, No. 7, pp. 537 to 539 (1968).
Noller, Chemistry of Organic Compounds, W. B. Saunders Co., Phila., pp. 147 and 148 (1966).

*Primary Examiner*—Helen M. S. Sneed
*Attorney, Agent, or Firm*—Connolly and Hutz

[57] ABSTRACT

Production of halogen-containing tertiary phosphine oxides of the general formula I

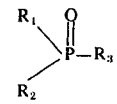

(I)

in which the substituents $R_1$, $R_2$ and $R_3$, being identical or different, stand for an alkyl, alkenyl, aryl or aralkyl radical, at least one of those radicals containing at least one aliphatically combined halogen atom. The compounds are made by reacting one or more compounds of the general formula II

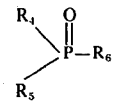

(II)

in which $R_4$, $R_5$ and $R_6$, being identical or different, stand for an alkyl, alkenyl, aryl or aralkyl radical, at least one of those $R_4$, $R_5$ and $R_6$ radicals containing an aliphatically combined hydroxyl group, with at least equivalent proportions, based on the number of hydroxyl groups, of gaseous hydrogen halide with agitation, if desired, at temperatures within the range about 100° and 300°C; freeing the reaction mixture, during the reaction or after termination thereof, from water originating from the reaction; and separating from the resulting reaction mixture the halogen-containing tertiary phosphine oxide by distillation or crystallization.

9 Claims, No Drawings

PRODUCTION OF HALOGEN-CONTAINING TERTIARY PHOSPHINE OXIDES

It has already been described (cf. K.A. PETROV, Z. H. Obshck, Khim. 35, 2062 (1965)) that dibutyl-hydroxymethylphosphine oxide can be reacted with thionyl chloride in accordance with the following reaction equation

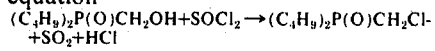

so as to obtain dibutyl-chloromethyl-phosphine oxide in a yield of 63.8%. In this reaction, it is necessary, per mol of phosphine oxide, to use one mol of sulfur dioxide and one mol of hydrogen chloride, which is disadvantageous as the latter two compounds are corrosive agents which have to be neutralized or disposed of.

A further process has been reported in German published Specification "Offenlegungsschrift" No. 2,060,217, wherein dialkyl-hydroxyalkyl-phosphine oxides are reacted with phosgene in accordance with the following reaction equation

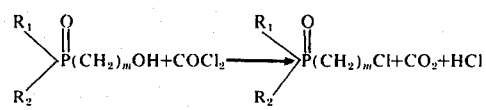

to produce the corresponding dialkyl-chloroalkyl-phosphine oxides.

Disadvantageous phenomena of this process reside in the use of very toxic phosgene and in the formation, per mol of phosphine oxide, of 1 mole of hydrogen chloride which has to be neutralized, expelled or disposed of.

The present invention now provides a process which is free from the disadvantageous phenomena referred to hereinabove.

The process of the present invention for making halogen-containing tertiary phosphine oxides of the general formula I

in which each of the substituents $R_1$, $R_2$ and $R_3$, being identical or different, stands for an alkyl, alkenyl, aryl or aralkyl radical, at least one of those radicals containing at least one aliphatically combined halogen atom, comprises reacting one or more compounds of the general formula II

in which $R_4$, $R_5$ and $R_6$, being identical or different, each stand for an alkyl, alkenyl, aryl or aralkyl radical, at least one of those $R_4$, $R_5$ and $R_6$ radicals containing an aliphatically combined hydroxyl group, with at least equivalent proportions, based on the number of hydroxyl groups, of gaseous hydrogen halide with agitation, if desired, at temperatures within the range about 100° and 300°C; freeing the reaction mixture, during the reaction or after termination thereof, from water originating from the reaction; and separating from the resulting reaction mixture the halogen-containing tertiary phosphine oxide by distillation or crystallization.

A preferred feature of the present process comprises making phosphine oxide derivatives of the general formula I, in which each of the substituents $R_1$, $R_2$, $R_3$, being identical or different, stands for an alkyl, halogenoalkyl, alkenyl, halogenoalkenyl radical having at most 18 carbon atoms, a phenyl, benzyl or mono, di- or tris(halogenoalkyl)-phenyl radical, the halogenoalkyl substituent of the phenyl radical having at most about 6 carbon atoms. The aliphatic halogen may be selected from chlorine or bromine, for example.

The starting materials containing hydroxyl groups are accordingly halogenated in accordance with the present invention with the preferred use of hydrogen chloride or hydrogen bromide. More preferably halogenated are those compounds of general formula II, in which the substituents $R_4$, $R_5$, $R_6$, being identical or different, stand for an alkyl, hydroxyalkyl, alkenyl, hydroxyalkenyl radical (having at most 18 carbon atoms) or phenyl, benzyl or mono-, di or tris(hydroxyalkyl)-phenyl radical, the hydroxyalkyl substituent of the phenyl radical having at most about 6 carbon atoms.

A further preferred feature of the process of the present invention comprises effecting the halogenation at temperatures within the range 130° and 250°C, at atmospheric pressure or under pressures up to about 20 atmospheres gauge. The reaction can be effected in the melt or in the presence of an inert solvent forming an azeotrope with water, such as xylene, p-chlorotoluene, trimethylbenzene, tetramethylbenzene, tetralin, decalin, decane or dodecane.

The final product is obtained in good yields by the use of between about 1 and 6 mols of hydrogen halide, per hydroxyl group in the starting material. Reaction water, which is liberated during the reaction, should conveniently be removed at the same rate as it is being formed. This can be done by continuous evaporation in those cases in which the reaction is effected in the melt and at atmospheric pressure. If the halogenation is effected in the presence of a solvent, it is good practice to remove the reaction water by distillation in the form of a solvent/water azeotrope. Hydrogen halide in excess, if any, can be stripped off after termination of the reaction, for example by flowing an inert gas through the reaction mixture.

In the present process, the phosphorus-containing alcohols have been found to react quantitatively with hydrogen halide. This is an unexpected result in view of WEYGAND-HILGETAG, Organisch-Chemische Experimentierkunst, Johann Amborsius Barth-Verlag, Leipzig, 3rd edition, 1964, page 299. It is reported therein that the reaction of aliphatic alcohols with hydrogen halide fails to be quantitative and that halide/alcohol mixtures are normally produced, which are commonly not separable into their components.

A further unexpected result resides in the fact that hydrogen halide is completely absorbed by the phosphorus-containing alcohol in the absence of any solvent at temperatures considerably higher than the melting point of the starting compounds.

It is possible for the process of this invention to be carried out at temperatures at which the phosphorus compounds having the hydroxyl groups therein already commence decomposition, in the absence of hydrogen halide. The present process should therefore be carried out with particular advantage in the melt and at atmospheric pressure.

The starting compounds of general formula II above are known or can be made by known methods, e.g., by the oxidation of suitable phosphines or by the additive combination of formaldehyde or unsaturated compounds with suitable phosphine oxides.

If carried out at atmospheric pressure, the present process can be effected in a heatable reactor provided with a thermometer, a hydrogen halide inlet opening into the reactor down to its bottom and, preferably, with an agitator. The reactor is connected to a heatable column and a condenser downstream thereof, for de-aeration. The reaction should preferably be effected at temperatures within the range 130° and 250°C. The reaction temperature to be selected depends on the thermal stability of the resulting halogenated phosphine oxide, as, e.g., halogenoalkyl-phosphine oxides having more than one carbon atom in the alkyl chain may tend to separate hydrogen halide at high temperatures with the resultant formation of the corresponding olefin.

The reaction of the present invention entails, per mol of hydroxyalkyl group being present in the phosphine oxide used, the formation of 1 mol of water, which is continually evaporated from the reaction mixture. In those cases in which the reaction is carried out in the presence of a solvent, the water is di-stilled off in the form of a solvent/water-azeotrope. It is therefore good practice to effect the present process at temperatures higher than 100°C. The column mounted above the reactor should conveniently be operated at temperatures within the range 110° and 160°C, this making it possible for the evaporating water or for the evaporating water/solvent-azeotrope to be maintained in vapor form, and for the reaction product evaporating from the reactor to be condensed and recycled thereinto.

The process of the present invention can more particularly be effected in the following manner, for example: A tertiary phosphine oxide containing hydroxyalkyl groups is placed in the reactor, heated therein to temperatures above its melting point, unless it is in the form of a melt, and thereafter heated, with agitation, to reaction temperature. During the initial heating period, hydrogen halide should preferably be introduced into the starting material so as to have an acid medium in the reaction mixture and to avoid decomposition of the starting material at higher temperature. Once the desirable reaction temperature has been reached, hydrogen halide is supplied per unit time in quantities which are completely absorbed by the reaction mixture. This is controlled by means of an off-gas meter, e.g., a bubble counter or rotameter, arranged downstream of the condenser. At the same time, the resulting reaction water, which is initially substantially free from hydrogen halide, is continually distilled off and collected downstream of the condenser. The high reaction velocity permits the supply per hour of a multiple of equivalents of hydrogen halide per equivalent of tertiary phosphine oxide containing hydroxyalkyl groups. Towards the end of the reaction, where the conversion is high, the quantity of hydrogen halide supplied per unit time at the onset of the reaction ceases to become completely absorbed. This is indicated by the passage of gas through the off-gas meter. If the conversion fails to be complete at that moment, it is necessary for the supply of hydrogen halide per unit time to be so reduced that the off-gas meter indicates slight gas flow. The reaction is terminated and an aqueous hydrohalic acid solution is obtained downstream of the condenser. As a result of this, only a slight overall excess of hydrogen halide, outside the ratio of hydrogen halide per hydroxyalkyl group of a tertiary phosphine oxide, is required to be used in the process of the present invention. In those cases in which a plurality of reactors in cascade arrangement are used, it is possible for unreacted hydrogen halide to be introduced together with fresh hydrogen halide into the next following reactor for further reaction therein.

A considerable advantage of the present process resides in the substitution of hydrogen halide for the very toxic thionyl chloride or phosgene compounds, particularly as 1 mol of hydrogen halide, which has to be disposed of, is set free per mol of each of these two latter compounds.

After termination of the reaction, it is possible for the reaction product having minor amounts of hydrogen halide dissolved or absorbed therein to be freed therefrom by stripping with an inert gas, e.g., nitrogen or carbon dioxide at temperatures within the range 100° and 250°C, or to be neutralized by treating the melt with an alkali metal or alkaline earth metal carbonate, e.g., $Na_2CO_3$, $K_2CO_3$ or $CaCO_3$. In this latter case, precipitated alkali metal or alkaline earth metal halide is filtered off and water originating from the neutralization is removed under vacuum. The resulting crude reaction product containing phosphine oxide can be purified by distillation under vacuum, recrystallization or in another manner.

The tertiary phosphine oxides produced in accordance with this invention are valuable intermediates which are able to transfer their water-solubilizing or interfacial or superfacial properties to products made therefrom. They can more particularly be used for making water-soluble pharmaceutical preparations.

EXAMPLE 1

A 4 l round flask placed in an oil bath and provided with a gas inlet opening thereinto down to its bottom, an agitator and a thermometer was fed with 3025 g or 28 mols of hydroxymethyl-dimethyl-phosphine oxide — briefly termed hereinafter HM-DMPO — which was rapidly heated therein to 190°C. At 110°C, gaseous hydrogen chloride was introduced in the quantity necessary to ensure complete absorption by the melt. It was found that the quantity of hydrogen chloride to be introduced increased considerably with an increasing temperature as indicated on the rotameter at various temperatures:

| Temp. in reaction mixture in °C | HCl-absorption indicated by rotameter l/h (standard conditions) |
| --- | --- |
| 110 | 125 |
| 140 | 157 |
| 180 | 750 |
| 190 | 1350 |

Water originating from the reaction was expelled via a packed column heated to 120°C and condensed in a cooler. The quantity of hydrogen chloride supplied was completely absorbed over a period of 40 minutes at 190°C. After that period, the off-gas was found to contain hydrogen chloride and an aqueous hydrochloric acid was obtained downstream of the cooler.

A sample of reaction mixture was taken and tested as to its composition using a Bruker HX-spectrometer, at 90 megahertz. The peaks showed a proton ratio of —$CH_2Cl$ : —$CH_2OH$ of 2.025 : 1. This corresponded to a conversion rate of 67%.

This was the moment where the quantity of hydrogen chloride to be supplied per hour was reduced down to 60–80 liters (standard conditions). After a further 2.5 hours at 190°C, the reaction was complete. A specimen was subjected to H-NMR spectroscopy, which indicated complete transformation of HM-DMPO to chloromethyl-dimethyl phosphine oxide.

EXAMPLE 2

3025 g (28 mols) of molten HM—DMPO was placed in the apparatus described in Example 1 and heated therein within 30 minutes from 120° to 235°C. During the initial heating period, hydrogen chloride was supplied at a rate of 60 l/h so as to provide for an acid medium and to avoid decomposition of HM-DMPO at high temperatures. Once the reaction mixture was at 235°C, hydrogen chloride was introduced thereinto over a period of 20 minutes at a velocity of 2500 l/h (standard conditions) which was substantially completely absorbed therein. Reaction water was found to distil off rapidly and simultaneously. After 20 minutes, the off-gas was found to contain hydrogen chloride. A sample of the reaction mixture was subjected to H-NMR-spectroscopy which indicated complete conversion of HM-DMPO to chloromethyldimethyl phosphine oxide.

The reaction product still contained 6.4 weight% of hydrogen chloride. Nitrogen was passed therethrough over a period of 4 hours at 220°C, whereby the hydrogen chloride concentration was reduced down to 3.1 weight%, and residual water was expelled. Altogether 599 g of an aqueous condensate was obtained. It contained 22.0 weight% of HCl.

To remove residual hydrogen chloride from the reaction product, the latter was mixed at temperatures within the range 100° and 110°C with an equivalent amount of $Na_2CO_3$, and precipitated NaCl was filtered off while hot. Following this, the water of neutralization was expelled under water jet vacuum and the residue was distilled at 132°C under 17 mm Hg. 3 328 g of colorless, crystalline chloromethyl-dimethyl phosphine oxide (ClM-DMPO) was obtained. The salt residue filtered off was treated with methylene chloride, the solvent was expelled and a further 112 g of ClM-DMPO was obtained.

Chloromethyl-dimethyl phosphine oxide was obtained in a total yield of 3 440 g corresponding to a 97% yield. The product melted at 66°C and had a $bp_{17}$ of 132°C.

EXAMPLE 3

A jacketed tube in upright position having a distilling column with a descending cooler mounted thereon was supplied with 166 g (1 mol) of 2-dimethylphosphinoxido-methyl-propane diol-1,3 of the formula $(CH_3)_2P(O)CH_2CH(CH_2OH)_2$, which was heated to 140°C. Gaseous hydrogen chloride was introduced from below through a glass frit at a rate of 80 g (2.2 mols) per hour. This corresponded to the supply of 53 l of HCl/hour at 25°C. Over a period of 1 hour, the hydrogen chloride was substantially completely absorbed by the reaction mixture, while the water set free was distilled off, almost completely free from hydrogen chloride. After that time, both the offgas and the condensate obtained downstream of the cooler had hydrogen chloride therein.

The reaction was complete after 3.5 hours. H-NMR spectroscopy indicated conversion of 54 weight% after 1 hour, of 92 weight% after 2 hours, and of 100 weight% after 3.5 hours of the diol compound used to 2-dimethylphosphinoxidomethyl-1,3-dichloropropane of the formula $(CH_3)_2P(O)CH_2CH(CH_2Cl)_2$.

EXAMPLE 4

166 g (1 mol) of 2-dimethylphosphinoxidomethyl-propane diol-1,3 was reacted with hydrogen chloride in the manner described in Example 3, but at 200°C. After 2 hours, the diol compound was found to have been completely transformed. H-NMR-spectroscopy indicated the formation of 77 mol% of 2-dimethylphosphinoxidomethyl-1,3-dichloropropane, $(CH_3)_2P(O)CH_2CH(CH_2Cl)_2$ and 23 mol% of 2-dimethylphosphinoxidomethyl-3-chloropropene-1, $(CH_3)_2P(O)CH_2C(CH_2Cl)=CH_2$.

EXAMPLE 5

155 g (1.14 mols) of dimethyl-3-hydroxypropyl-phosphine oxide was reacted with hydrogen chloride in the apparatus described in Example 3. The melt was heated to 160°C and 80 g (2.2 mols) of gaseous hydrogen chloride was introduced per hour thereinto. This corresponded to the supply of 53 l of HCl per hour at 25°C. Within the first 30 minutes, the reaction heat established a temperature within the range 170° and 180°C, in the reaction mixture. Over a period of 50 minutes, the hydrogen chloride was completely absorbed by the reaction mixture, while the water set free was distilled off simultaneously. Samples were taken during the reaction and subjected to H-NMR-spectroscopy which indicated conversion of 87.5 weight% after 50 minutes, of 96 weight% after 170 minutes and of 98 weight% after 230 minutes, of the starting material to dimethyl-3-chloropropyl-phosphine oxide $(CH_3)_2P(O)CH_2CH_2CH_2Cl$.

EXAMPLE 6

1000 g of dimethyl-hydroxymethyl phosphine oxide was placed in an acidproof 4 l autoclave provided with a stirrer and melted therein at a temperature within the range 100° and 120°C. The temperature was increased to 160°C and hydrogen chloride was introduced until a pressure of 4 atmospheres gauge was found to have been established in the autoclave. After a few minutes, the pressure decreased and was then kept constant by the introduction of a further 100 g of hydrogen chloride. After a further 3 hours, a further 100 g of hydrogen chloride were introduced whereby the pressure increased up to 8 atmospheres gauge. Under that pressure and at a temperature of 160°C, the reaction mixture was stirred for a further 1 hour, cooled with pressure relief and distilled under a vacuum of 12 mm Hg. Dimethyl-chloromethyl-phosphine oxide ($bp_{12}$ = 116°–120°C) was obtained in a yield of 946 g or 81% of the theoretical.

EXAMPLE 7

A solution of 108 g of dimethyl-hydroxymethyl-phosphine oxide in 300 cc of xylene was reflux boiled and hydrogen chloride was introduced into the solution. After about 18 hours, 18 cc of a water/solvent-azeotrope was separated from the reaction mixture, which was distilled under a vacuum of 15 mm Hg. Dimethylchlormethylphosphine oxide (bp$_{15}$ = 128°–130°C) was obtained in a yield of 100 g or 79.5% of the theoretical.

If p-chlorotoluene is used as the solvent, it is possible for the reaction period to be shortened to about 8 hours.

EXAMPLE 8

Hydrogen chloride was introduced over a period of 14 hours into a suspension of 31 g of dihydroxymethyl-methyl-phosphine oxide (having a purity of 93%) in 100 cc of xylene. The suspension had a temperature of 140°C. 9 cc of reaction water was formed which was removed distillatively as a xylene/water-azeotrope, from the reaction mixture. After the reaction was complete, the solvent was distilled off under water jet vacuum and the residue was subjected to fractional distillation under vacuum. Dichloromethyl-methyl-phosphine oxide (bp$_{0.3}$ = 122°C) was obtained in a yield of 30.5 g or 81.5% of the theoretical.

EXAMPLE 9

Hydrogen chloride was introduced over a period of 6 hours at 140°C into a solution of 23 g of dipropyl-hydroxymethyl-phosphine oxide in 100 cc of xylene and the resulting reaction water was removed distillatively as a xylene/water azeotrope, from the reaction mixture. After termination of the reaction, the reaction mixture was distilled under water jet vacuum and chloromethyl-diisopropyl-phosphine oxide (bp$_{11}$ = 145°–147°C) was obtained in a yield of 20.5 g or 80% of the theoretical.

EXAMPLE 10

140 g (1 mol) of tris-hydroxymethyl-phosphine oxide was placed in a 250 cc round flask provided with a gas inlet, melted therein at 50°–60°C and heated to 160°C while HCl gas was introduced thereinto in a quantity of 20 l/h (standard conditions). The resulting reaction water was expelled through a tube heated to 113°C and condensed in a cooler. After 10 hours, condensate ceased to be formed. The reaction was interrupted and the reaction mixture was cooled. 192 g of a colorless crude product and 85 g of condensate containing 40 weight% of HCl were obtained.

After recrystallization from carbon tetrachloride, colorless tris-chloromethyl-phosphine oxide melting between 97° and 100°C was obtained in a yield of 155 g or 79.2%.

EXAMPLE 11

The procedure was the same as that described in Example 6 save that the crude product (194 g) was purified by subjecting it to distillation under vacuum. 154 g of tris-chloromethyl-phosphine oxide (fp = 96°–98°C) distilled over under a pressure of 0.01 mm Hg at temperatures within the range 125° and 126°C. The product was free from hydrogen chloride but contained 0.04 val/100 g of an unidentified acid.

We claim:

1. A process for making halogen-containing tertiary phosphine oxides of the general formula I

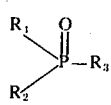

in which the substituents R$_1$ and R$_2$ being methyl, propyl or chloromethyl and R$_3$ stands for chloromethyl-, chloropropyl or

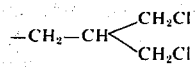

which comprises reacting a compound of the general formula II

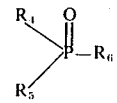

in which R$_4$ and R$_5$ stand for methy, propyl or hydroxymethyl and R$_6$ being hydroxymethyl, hydroxypropyl or

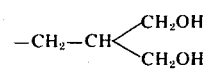

with at least equivalent proportions, based on the number of hydroxyl groups, of gaseous hydrogen chloride at temperatures within the range about 100° and 300°C; freeing the reaction mixture, during the reaction or after termination thereof, from water originating from the reaction; and separating from the resulting reaction mixture the halogen-containing tertiary phosphine oxide by distillation or crystallization.

2. The process as claimed in claim 1, wherein the reaction is effected at temperatures within the range 130° and 250°C.

3. The process as claimed in claim 1, wherein the reaction is effected at atmospheric pressure or under overpressure up to about 20 atmospheres gauge.

4. The process as claimed in claim 1, wherein the reaction is effected in the melt or in the presence of an inert solvent forming an azeotrope with water.

5. The process as claimed in claim 4, wherein the solvent is selected from xylene, p-chlorotoluene, trimethylbenzene, tetramethylbenzene, tetralin, decalin, decane or dodecane.

6. The process as claimed in claim 1, wherein about 1 to 6 mols of hydrogen chloride are used per hydroxyl group in the starting material.

7. The process as claimed in claim 1, wherein the reaction is effected in the melt and resulting reaction water is continually removed at atmospheric pressure, from the reaction mixture.

8. The process as claimed in claim 1, wherein the reaction is effected in the presence of a solvent and the resulting reaction water is continually removed in the form of a solvent/water-azeotrope, from the reaction mixture.

9. The process as claimed in claim 1, wherein hydrogen chloride in excess is stripped off by flowing an inert gas through the reaction mixture, after termination of the reaction.

* * * * *